(12) United States Patent
Hoheisel et al.

(10) Patent No.: US 7,447,295 B2
(45) Date of Patent: Nov. 4, 2008

(54) METHOD AND TOMOGRAPHY UNIT FOR THE RECONSTRUCTION OF A TOMOGRAPHIC DISPLAY OF AN OBJECT

(75) Inventors: Martin Hoheisel, Erlangen (DE); Wolfgang Harer, Erlangen (DE); Holger Kunze, Bubenreuth (DE); Karl Stierstorfer, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 5 days.

(21) Appl. No.: 11/584,544

(22) Filed: Oct. 23, 2006

(65) Prior Publication Data
US 2007/0093711 A1 Apr. 26, 2007

(30) Foreign Application Priority Data
Oct. 24, 2005 (DE) .................. 10 2005 050 917

(51) Int. Cl.
*H05G 1/60* (2006.01)
(52) U.S. Cl. .......................................... 378/4
(58) Field of Classification Search ........... 378/4–20, 378/207, 901
See application file for complete search history.

(56) References Cited

U.S. PATENT DOCUMENTS

| | | | | |
|---|---|---|---|---|
| 4,494,141 A | * | 1/1985 | Altekruse | 378/19 |
| 4,649,561 A | * | 3/1987 | Arnold | 378/207 |
| 4,729,100 A | | 3/1988 | Tsujii | |
| 5,105,451 A | * | 4/1992 | Lubinsky et al. | 378/28 |
| 5,384,861 A | * | 1/1995 | Mattson et al. | 382/131 |
| 5,745,542 A | * | 4/1998 | Gordon et al. | 378/4 |
| 5,848,114 A | * | 12/1998 | Kawai et al. | 378/4 |

(Continued)

FOREIGN PATENT DOCUMENTS

DE 10037491 A1 2/2002

(Continued)

OTHER PUBLICATIONS

Andia et al., Nonlinear Sinogram Filter Design for Backprojection Reconstruction, IEEE, 2000, vol. 2, pp. 15/179-15/183.*

(Continued)

*Primary Examiner*—Edward J. Glick
*Assistant Examiner*—Alexander H Taningco
(74) *Attorney, Agent, or Firm*—Harness, Dickey & Pierce

(57) ABSTRACT

A method is disclosed for reconstructing a tomographic representation of an object from projection data off a moving radiation source through this object onto a detector, filtering and back projection of the projection data being executed in the reconstruction. In an embodiment of the method, by using at least one identical spatial arrangement of the radiation source, the detector and a test object instead of the object to be scanned, there is determined by test projections and an iterative reconstruction technique, a filter that in the given arrangement results in an optimum filtering and back projection of the projection data of the test object for the tomographic representation. Further, the object is scanned instead of the test object in the given arrangement and projection data are determined. Finally, the reconstruction of the tomographic representation is carried out using these projection data and the filter determined. Moreover, an embodiment of a tomography unit for carrying out this method is also disclosed.

40 Claims, 4 Drawing Sheets

U.S. PATENT DOCUMENTS

| | | | | |
|---|---|---|---|---|
| 5,881,162 | A | * | 3/1999 | Ishimitsu ..................... 382/132 |
| 5,909,476 | A | * | 6/1999 | Cheng et al. .................... 378/4 |
| 6,285,733 | B1 | * | 9/2001 | Proksa et al. ................. 378/15 |
| 6,426,988 | B2 | * | 7/2002 | Yamada et al. ................. 378/4 |
| 6,529,575 | B1 | * | 3/2003 | Hsieh ............................ 378/4 |
| 6,973,157 | B2 | * | 12/2005 | Claus ............................ 378/8 |
| 7,006,594 | B2 | * | 2/2006 | Chell et al. ................... 378/18 |
| 7,167,738 | B2 | | 1/2007 | Schweikard et al. |
| 2003/0194049 | A1 | * | 10/2003 | Claus et al. ................... 378/22 |
| 2004/0114707 | A1 | | 6/2004 | Bruder et al. |
| 2005/0058240 | A1 | * | 3/2005 | Claus .......................... 378/22 |
| 2005/0259780 | A1 | * | 11/2005 | Goodgame et al. ............. 378/4 |
| 2006/0002509 | A1 | * | 1/2006 | Claus et al. ................... 378/21 |
| 2007/0053556 | A1 | * | 3/2007 | Nielsen et al. .............. 382/128 |

FOREIGN PATENT DOCUMENTS

| | | |
|---|---|---|
| DE | 10244181 A1 | 4/2004 |
| JP | 10146334 A | 6/1998 |
| WO | WO 2005036466 A1 | 4/2005 |

OTHER PUBLICATIONS

Subbarao et al., Performance of iterative tomographic algorithms applied to non-destructive evaluation with limited data, NDT&E International, 1997, vol. 30, No. 6, pp. 359-370.*

Andersen et al., Simultaneous Algebraic Reconstruction Technique (SART): A Superiour Implementation of the ART Algorithm, Ultrasonic Imaging 6, 1984, pp. 81-94.*

Tao Wu et al.: "Digital Tomosynthesis Mammography Using a Parallel Maximum Likelihood Reconstruction Method", Medical Imaging 2004: Physics of Medical Imaging, Proceedings of SPIE vol. 5368 (2004), pp. 1-11.

Thorsten M. Buzug: "Einführung in die Computertomographie", Springer Verlag, ISBN 3-540-20808-9, 2004, pp. 134-138, pp. 153-170, pp. 189-193.

Kak, Slaney: "Principles of Computerized Tompgraphic Imaging", IEEE Press, ISBN 0-87942-198-3, 1987, pp. 49-112.

Kachelrieβ M., Knaup M., Kalender W.A.: „Phase-Correlated Imaging from Multithreaded Spiral Cone-Beam CT Scans of the Heart, International Meeting on Fully Three-Dimensional Image Reconstruction, Salt Lake City; Utah, USA; Prceedings of Fully 3D, Jul. 6-9, 2005, pp. 159-162.

Kao C.-M. et al.: "Accurate Image Reconstruction for DOI-PET Systems an Its Implications for the Development of Economic, Compact PET (ezPET) Systems" Nuclear Science Symposium 1999 IEEE Oct. 24-30, 1999, Piscataway, NJ, USA pp. 1363-1367; Others.

* cited by examiner

METHOD AND TOMOGRAPHY UNIT FOR THE RECONSTRUCTION OF A TOMOGRAPHIC DISPLAY OF AN OBJECT

PRIORITY STATEMENT

The present application hereby claims priority under 35 U.S.C. §119 on German patent application number DE 10 2005 050 917.7 filed Oct. 24, 2005, the entire contents of which is hereby incorporated herein by reference.

FIELD

The invention generally relates to a method for reconstructing a tomographic representation of an object. For example, it may relate to a method for reconstructing a representation from projection data of a moving radiation source onto a detector, with filtering and back projection of the projection data being executed in the reconstruction. Moreover, the invention generally relates to tomography units; for example ones where projections are obtained by using different radiation.

BACKGROUND

Computed tomography (CT) provides a diagnostic and measuring method for medicine and test engineering with the aid of which internal structures of a patient or test object can be examined without needing in the process to carry out surgical operations on the patient or to damage the test object. In this case, there are recorded from various angles a number of projections of the object to be examined from which it is possible to calculate a 3D description of the object.

It is generally known to solve this problem by using the so called filtered projection (filter back projection FBP), the following documents being referenced by way of example [Bu04]: Buzug: "Einführung in die Computertomographie" ["Introduction to computed tomography"], 1st edition 2004, Springer-Verlag, ISBN 3-540-20808-9 and [KS84] Kak, Slaney: "Principles of Computerized Tomographic Imaging", 1987, IEEE Press, ISBN 0-87942-198-3. FBP is a high performance computing method in which measured projections are filtered and back projected onto the image.

In this method, the image quality depends on the applied filters or convolution cores. These can be specified exactly in analytical terms for simple scanning geometries. Essentially, these are circular paths in the case of which many projections are recorded in uniform angular steps. More complex recording geometries that violate these assumptions lead to problems when attempting to determine the filters analytically. An example of this is tomosynthesis, where in the most general case only a few projections are obtained on a free path from a restricted angular distance.

Iterative methods such as the algebra reconstruction method (ART) have proved their worth for such reconstruction problems. Reference is made in this regard to the following documents [Bu04]: Buzug: "Einführung in die Computertomographie" ["Introduction to computed tomography"], 1st edition 2004, Springer-Verlag, ISBN 3-540-20808-9 and [KS84] Kak, Slaney: "Principles of Computerized Tomographic Imaging", 1987, IEEE Press, ISBN 0-87942-198-3 and [WZM04] T. Wu, J. Zhang, R. Moore, E. Rafferty, D. Kopans, W. Meleis, D. Kaeli: "Digital Tomosynthesis Mammography Using a Parallel Maximum Likelihood Reconstruction Method", Medical Imaging 2004: Physics of Medical Imaging, Proceedings of SPIE Vol., 5368 (2004) 1-11. It is advantageous in the case of this ART that iterative methods require no filters such as are necessary in the case of FBP. Because of their iterative nature, however, their computational period is substantially longer and is therefore often not feasible in practice. A further disadvantage of ART resides in the fact that by contrast with FPB this method cannot be used for any construction of subregions of the object (reasons of interest, ROI).

Reference is made by way of addition to patent application US 2005/0058240 A1, in which the inventor calculates reconstruction filters analytically by using very greatly simplifying, heuristic assumptions. The method is therefore limited to a few simple recording geometries and, moreover, to tomosynthesis.

The problem therefore exists of finding an efficient method for reconstruction of tomographic representations of an object from projection data that, on the one hand, does not place excessively high requirements on the computing power required for the reconstruction but, on the other hand, can also be used for any desired recording geometries and relative movements between radiation source, detector and object during the measurement.

SUMMARY

In at least one embodiment of the invention, a method is presented that reduces or even eliminates at least one of the above-named problems.

The inventors, in at least one embodiment, have realized that in the case of digital imaging, more precisely when obtaining three-dimensional images of volumetric data from one- or two-dimensional recorded projections, or two-dimensional images from one-dimensional projections, it is possible to obtain digital filters for any desired scanning geometries from an iterative method, preferably ART. The filters can then be used for the reconstruction in accordance with the FBP method.

By using a specific spatial arrangement of the radiation source, the detector and a test object instead of the object to be scanned, there is determined per projection with the aid of projections of the test object and with the aid of an iterative reconstruction technique, a filter that for the given arrangement, results in an optimum filtering and back projection of the projection data of the test object for the tomographic representation. This filter thus determined is subsequently used for the reconstruction by filtering and back projection of projection data of an examination object that has been scanned instead of the test object in the given arrangement. It is true that the calculation of the correct filter is computation-intensive in this case, but it is performed only once for a given scanning geometry. The computational outlay for FBP with this given filter does not differ from the classic FBP.

By comparison with the classic FBP, this method offers the possibility of generating and using for any desired scanning geometries filters that are matched to the problem. A substantial increase in speed is achieved by comparison with ART. In addition, the method offers the possibility of selectively reconstructing sub-regions of the object (region of interest, ROI) as known from classic FBP.

This method, in at least one embodiment, is capable in principle of being applied both for tomographic representations and for tomosynthesis, and can be used for all imaging tomographic methods independently of the type of radiation.

In accordance with the above finding, the inventors propose, in at least one embodiment, to improve the method known per se for the reconstruction of a tomographic representation of an object from projection data of a moving radiation source through this object onto a detector, in the case of which filtering and back projection of the projection data are executed for the reconstruction, to the effect that by using at least one identical spatial arrangement of the radiation source, the detector and a test object instead of the object to be scanned, there is determined by test projections and an iterative analytical reconstruction technique a filter that in the given arrangement results in an optimum filtering and back projection of the projection data of the test object for the tomographic representation, the object is scanned instead of the test object in the given arrangement and projection data are determined, and the reconstruction of the tomographic representation is carried out using these projection data and the filter determined.

According to at least one embodiment of the invention, both at least 2D sectional representation or a 3D volumetric representation of the object can be reconstructed. Moreover, 1D projections or 2D projections can be used to determine the filter and for the reconstruction.

There are no limitations as to the recording geometry, and the projections can be recorded by way of example using fan beam geometry or conical beam geometry. Usually, the radiation source and the detector move on a circular or spiral path relative to the scanned object. However, these paths can be freely selected in at least one embodiment of this method.

It is also possible to use the measured data to carry out a rebinning such that the projection data are present for the reconstruction using parallel beam geometry, for example.

A further feature of this method, according to at least one embodiment of the invention, is that in order to be acquired the object can be scanned using an angular distance <180 degrees.

Furthermore, it is possible in this method, in at least one embodiment, to scan the object at relatively large angular spacings, for example an angular spacing of at least 2° between the projections is possible. Then, scanning can be performed with a variable increment between the individual measured projections.

Particularly when the path of the radiation source follows a noncircular curve, a dedicated filter is advantageously determined for each projection angle and used in the reconstruction. Accordingly, it is also possible to determine a dedicated filter for each projection site of the radiation source and/or the detector, and to use it in the reconstruction. This filter can also be spatially dependent in the most general case.

Measurements can advantageously be carried out on at least one test object in order to determine the filter to be used, or projections can be calculated on simulated test objects.

The test object should contain as many spatial frequencies as possible. It is therefore advantageous to make use of one or more wires or an arrangement of small balls, for example. In addition to the abovenamed test objects, noise, balls or rods with the Gaussian density distribution, for example, are suitable as simulated test objects.

In order to avoid an excessively large storage requirement in the computer system respectively used, it can be advantageous when a smaller number of new, averaged filters are calculated from the originally iteratively determined filters by averaging them over sites and/or projection angles. If such filters of reduced number are used, or if what is already originally present is only filters at jumps larger than projections measured during the actual scan, it is possible to calculate filters for a specific site and/or a specific projection by interpolating between filters that belong to other sites and/or projections.

In accordance with at least one embodiment of the invention and the method described above, the latter can be applied for any type of tomography units, but in particular for a tomography unit in which projections are obtained from x ray imaging, from magnetic resonance imaging, from ultrasound imaging or else from optical imaging. The inventors, in at least one embodiment, further propose for such tomography units that a data memory be present in which the predetermined filter can be stored long term.

Particularly in the case of applications in large clinics, it is also advantageous to provide programs that transmit the determined projection data and, in addition, the stored filters to a separate image computer.

BRIEF DESCRIPTION OF THE DRAWINGS

The invention, in particular also the mathematical principles for the filter calculation, is described below in more detail, using example embodiments, with the aid of the figures, only the features required to understand the invention being illustrated. Use is made for this purpose of the following reference numerals: 11: x ray source at a first position; 11': x ray source at another position; 12: x ray beam of a first projection; 12': x ray beam of another projection; 13: detector at a first position; 13': detector at another position; 14: reconstruction field; 15: evaluation computer; 16: display unit; 17: memories for filters; 18: object/patient; 21: measured projections; 22: filtering/convolution; 23: filtered projections; 24: filters; 25: back projection; 26: image/volume data; 31: measured projections; 32: initial image; 33: changed projections after the nth iteration; 34: reconstructed image after the nth iteration; 35: calculation of the calculated projections (projector); 36: determining the difference between calculated projections and measured projections; 37: summation between difference and varied projections; 38: back projection of the varied projections (back projector); 41: measured projections; 42: iteratively varied projections; 43: algorithm; 44: filters; 51: x ray source; 53: detector; 54: reconstruction region; 58: wire model; 61: x ray source; 62: x ray beam; 63: detector; 65: evaluation computer; 66: display unit; 67: memories for filters; 68: thorax; 69: compression plate.

In detail.

DETAILED DESCRIPTION OF THE EXAMPLE EMBODIMENTS

Figure 1:
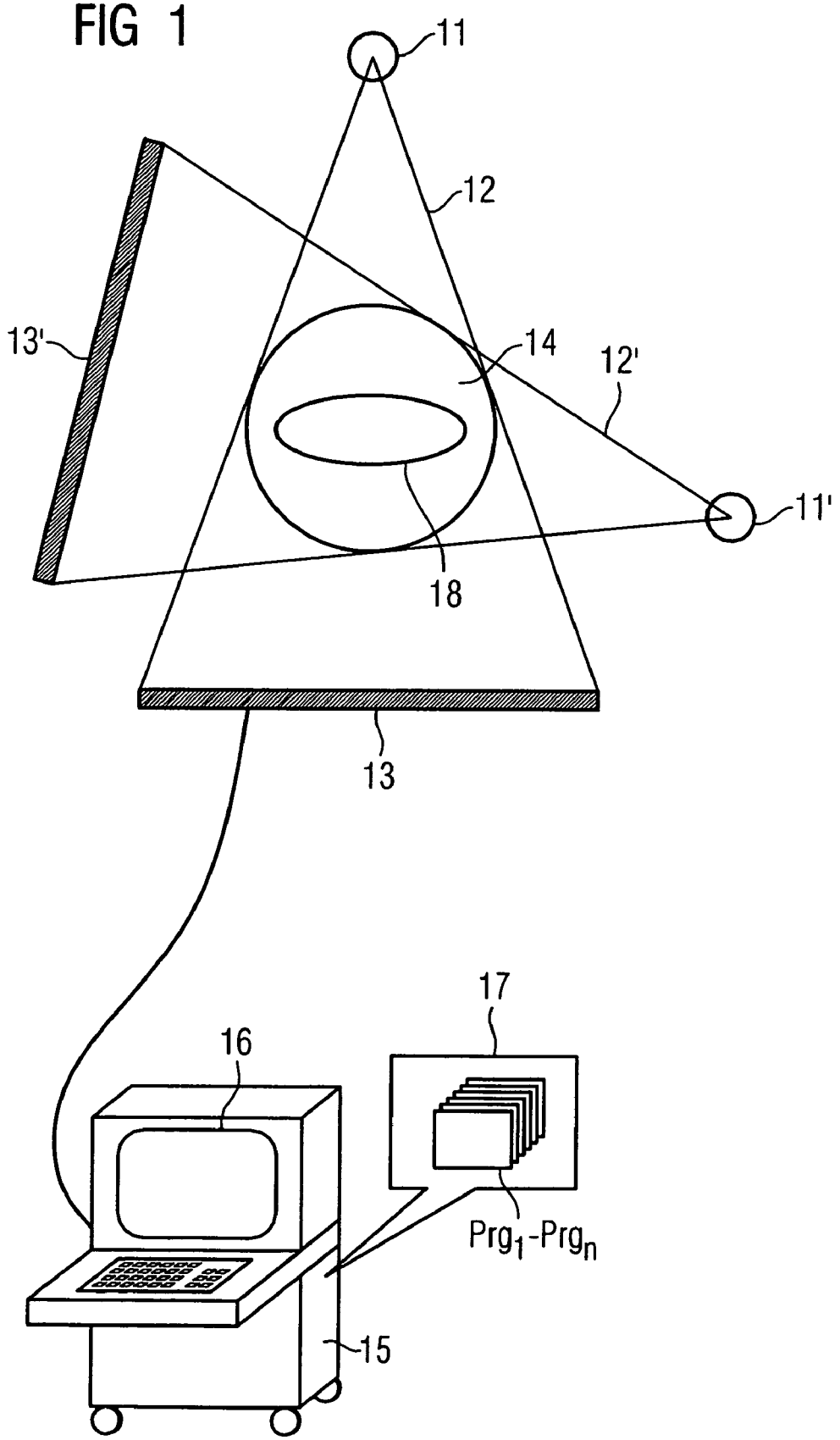
FIG. 1: shows a typical CT arrangement with an x ray source.

The terminology used herein is for the purpose of describing particular embodiments only and is not intended to be limiting of the present invention. As used herein, the singular forms "a", "an" and "the" are intended to include the plural forms as well, unless the context clearly indicates otherwise. It will be further understood that the terms "includes" and/or "including", when used in this specification, specify the presence of stated features, integers, steps, operations, elements, and/or components, but do not preclude the presence or addition of one or more other features, integers, steps, operations, elements, components, and/or groups thereof.

In describing example embodiments illustrated in the drawings, specific terminology is employed for the sake of clarity. However, the disclosure of this patent specification is not intended to be limited to the specific terminology so selected and it is to be understood that each specific element includes all technical equivalents that operate in a similar manner.

Referencing the drawings, wherein like reference numerals designate identical or corresponding parts throughout the several views, example embodiments of the present patent application are hereafter described.

FIG. 1 shows a known typical CT arrangement with an x ray source 11, in a first position, that emits for a first projection an x ray beam 12 that is detected in a detector 13 at this first position after it has penetrated the object, here a patient 18, lying in the reconstruction field 14 and to be examined. The data of the detector pass into an evaluation computer 15 that undertakes the reconstruction, and are subsequently displayed on a display unit 16. The x ray source 11 moves here in an ideal way on a circular path, numerous projections being recorded from different angles. The x ray source 11' is also illustrated in FIG. 1 in another angular position, the x ray beam 12' being emitted for another projection that is then detected in the detector 13' at this other position.

Figure 2:
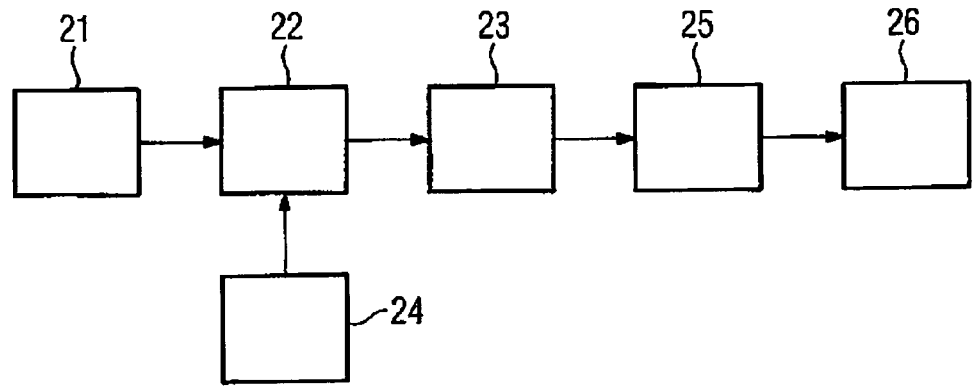
FIG. 2: shows a flowchart of the calculation rule of an FBP.

The standard reconstruction method of such a CT arrangement is filtered back projection (FBP). Before the calculation, a sorting (rebinning) of the beams is further undertaken, for the most part, before the calculation such that a set of projections with parallel beams at equidistant projection angles is to hand. In this simplest case of parallel beams and a circular, equidistantly scanned scanning path, the calculating rule of the FBP can be subdivided into two steps that are illustrated schematically in FIG. 2:

1. convolution 22 of the projection data 21 with the aid of a filter 24, identical for all the projections, with a frequency response |w|, |w| being the magnitude of the frequency of the Fourier transforms of the projections.
2. Back projection 25 of the filtered projections 23 onto the finished image or the volume data 26.

If the beams emanate in the shape of a cone from a focus, either a geometrically dependent weighting of the data or their resorting into parallel beams is required before the convolution (rebinning). A geometrically dependent modification of the filter can be required, in addition. Detailed descriptions of the algorithms are to be found in [KS84] Kak, Slaney: "Principles of Computerized Tomographic Imaging", 1987, IEEE Press, ISBN 0-87942-198-3 and [Bu04] Buzug: "Einführung in die Computertomographie" ["A reduction to computed tomography], 1st edition 2004, Springer-Verlag, ISBN 3-540-20808-9. Filters of acceptable complexity can no longer be specified analytically for general scanning geometries.

The FBP can be formulated mathematically with the aid of the equation:

$$X = R\,W\,Y,\qquad \text{eq. (1)}$$

the vector sought for the object to be reconstructed being designated by X, the back projection matrix by R, and the vector of the measured projection data by Y. The matrix W contains the combination of filtering and weighting, and is defined below as filter, for short.

The iterative ART method according to an embodiment of the invention for determining the filter that is to be used optimally in the following FBP is based on the principle that the measured projections are compared with the projections calculated from an object already reconstructed, and the error is subsequently used to correct the image of the object. In this case, the image is calculated in the nth iteration $X_n$ with the aid of the update equation $$X_n = X_{n-1} + R\,V\,(Y - P\,X_{n-1}).\qquad \text{eq. (2)}$$

There is a suitable initial image $X_0$, for example a zero image, at the beginning of the iteration. P in this case represents the system matrix with the aid of which the projections are calculated from the scanned object image using knowledge of the scanning geometry. V is a conditioning matrix with the aid of which the convergence rate can be influenced. For the simplest case, it is a diagonal matrix with identical values for example the value 1.

This description of ART that is common in the literature can be rewritten as follows, $X_{n-1}$ being represented here as a back projection of "corrected data" $Y_{n-1}$:

$$X_{n-1} = R\,Y_{n-1},\qquad \text{eq. (3)}$$

such that formula (2) can be rewritten as follows $$\begin{aligned}X_n &= R\,Y_{n-1} + R\,V\,(Y - P\,R\,Y_{n-1})\\ &= R\,(Y_{n-1} + V\,(Y - P\,R\,Y_{n-1}))\\ &= R\,((1 - V\,P\,R)Y_{n-1} + V\,Y).\end{aligned}\qquad \text{eq. (4)}$$

It follows for $Y_n$ that $$Y_n = (1 - V\,P\,R)Y_{n-1} + V\,Y = K\,Y_{n-1} + V\,Y\qquad \text{eq. (5)}$$

where $$K = (1 - V\,P\,R).\qquad (6)$$

The recursive expression in eq. (5) can be transformed into the explicit expression $$Y_n = K^n Y + \frac{K^n - 1}{K - 1}Y = \left(K^n + \frac{K^n - 1}{K - 1}\right)Y = U_n Y\qquad \text{eq. (7)}$$

This shows that $Y_n$ emerges from Y by a matrix operation.

Comparison of eq. (3) and eq. (7) with eq. (1) indicates that $U_n$ must correspond to the FBP filter matrix W of eq. (1) that carries out the filtering and weighting of the data in FBP. The optimum filter, which can be used for a specific projection and a given scanning geometry in an FBP can therefore be found for this projection by an iterative analytical reconstruction with the aid of a previously known object.

Figure 3:
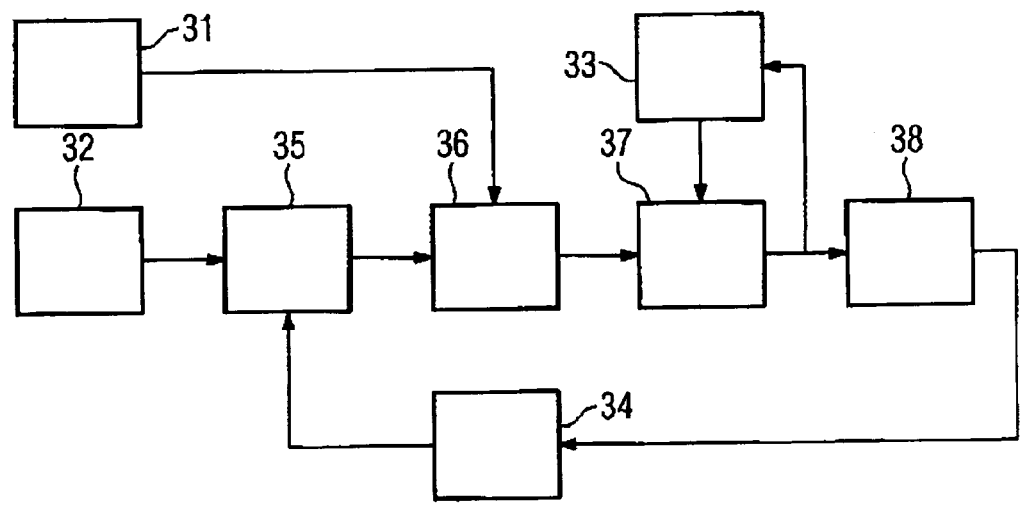
FIG. 3: shows a flowchart of the iterative reconstruction.

The process of the iterative reconstruction is illustrated in FIG. 3. The projector 35 is used to determine calculated projections from an initial image 32. The difference 36 between the calculated projections and the measured projections 31 is subsequently formed and added to the changed projections 33 in block 37. This sum is, firstly, subsequently stored in 33 and, secondly, back projected in 38. The calculated projections are determined in the second iteration from the image 34 thus obtained. This iteration is now carried out until convergence is reached or the algorithm is truncated. The process must be initialized such that the projections whose simple back projection produces the initial image 32 are stored in 33 at the beginning. Element 33 includes only values 0 in the case of a zero image.

The filters thus obtained are adapted to the reconstruction problem to be solved on the basis of their design. Generally, weighting and filtering vary with site and are mostly a function of the projection currently being considered. However, in many cases the filters will change only slowly with the site and the projection, and so it frequently suffices to reduce their number by averaging over suitable site regions or projection regions. It is also possible to interpolate between filters relating to different site regions and projection regions.

Experience with iterative reconstruction indicates that the filters $U_n$ belonging to intermediate steps can also have advantageous reconstruction properties.

An analytical or direct calculation of U or $U_n$ is mostly impossible owing to the complexity and, overall the size of the projection and back projection matrices.

Instead of this, according to an embodiment of the invention the filters are calculated for a prescribed recording geometry by determining the transfer function $U_n$ as a function of site and projection.

As a first step for calculating the filters, it is necessary to determine projections Y for a given scanning geometry. In one application, this can be done by measuring the projections of suitable measuring objects such as, however, thin wires in the CT system. In another application, the projections can be determined by simulating the same objects in the desired scanning geometry.

The object to be imaged can be reconstructed iteratively in accordance with eq. (5) using the projections thus obtained. In this case, the iteration is truncated whenever a desired image sharpness or a desired signal-to-noise ratio is reached. After this iteration step, the filters $U_n$, which are generally a function of site, can be determined with the aid of generally known methods by comparing the $Y_n$ and Y. Reference is made in this context to the document [OS75] Oppenheim, Alan V. Schafer, Ronald: "Digital Signal Processing", Prentice Hall, 1975, ISBN 0132146355, the entire contents of which are hereby incorporated herein by reference.

A few examples of the determination of $U_n$ are given below. If, for example, the test object is a thin wire, this can be interpreted in terms of system theory as an impulse. The site-dependent transfer function $U_n$ can then easily be obtained from the corrected projections $Y_n$. The site- and projection-dependent determination of $U_n$ can be made by a repeated measurement using a number of offset wires.

In the case of general test objects, $U_n$ can be determined wit the aid of short time Fourier transformation for example.

In a further implementation, the projections can also include simulated or measured noise. $U_n$ can then be determined by means of the local autocorrelation function, for example. Reference may be made to this end to document [OS75] Oppenheim, Alan V. Schafer, Ronald: "Digital Signal Processing", Prentice Hall, 1975, ISBN 0132146355.

Figure 4:
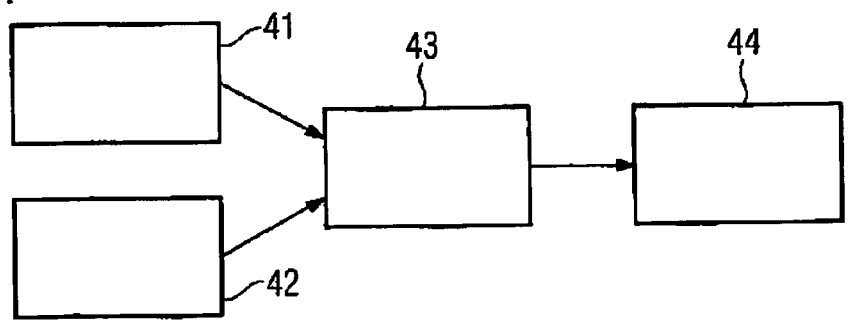
FIG. 4: shows a schematic description of the filter calculation.

A schematic description of the filter calculation is shown in FIG. 4. An algorithm 43 adapted to the projections is used here to calculate the filters 44 from the measured projections 41 and the projections 42 varied iteratively therefrom.

Figure 5:
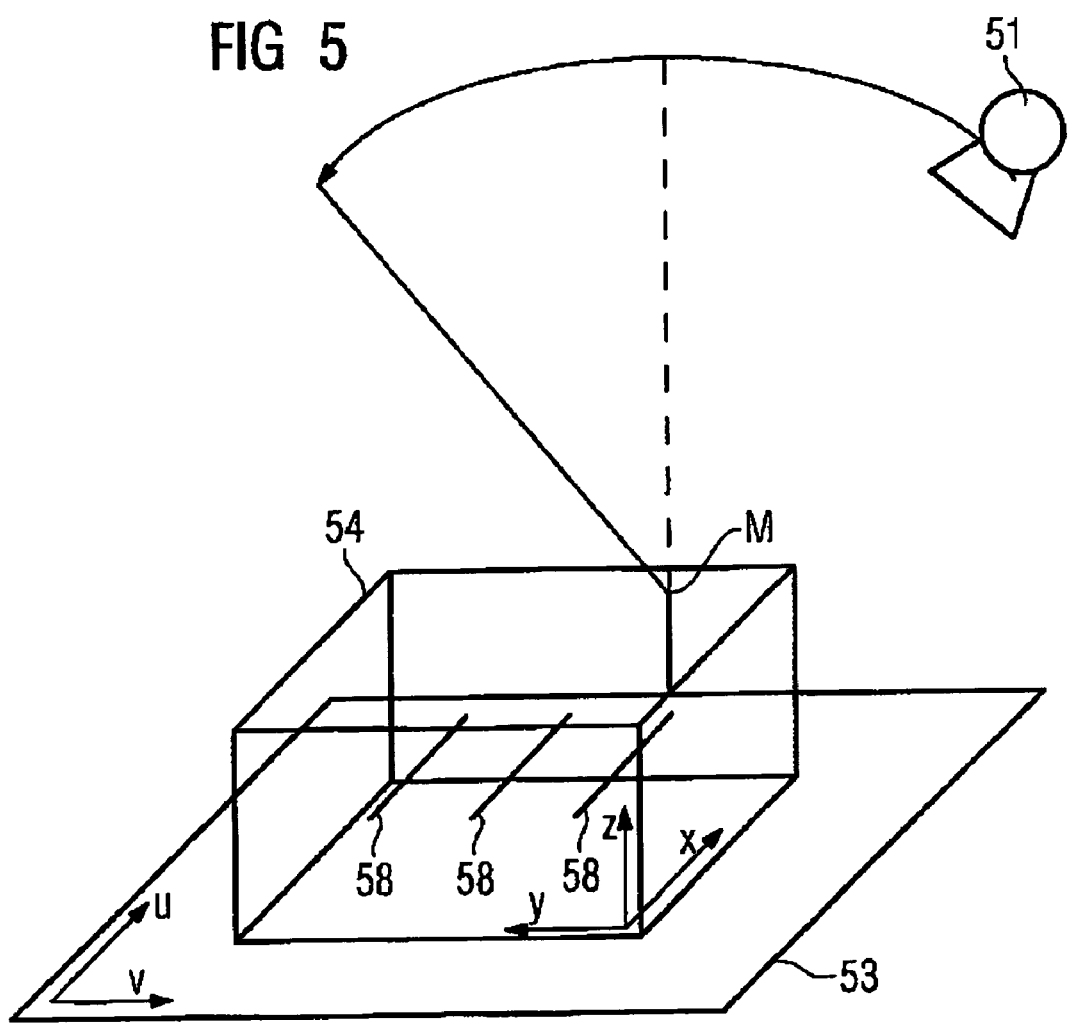
FIG. 5: shows the recording geometry of a mammography system.

As already mentioned above, the method according to an embodiment of the invention is suitable, for example, for application in a tomosynthesis in mammography. FIG. 5 shows by way of example in this context a schematic 3D view of the recording geometry of an x ray source 51, a flat detector 53 and a wire phantom 58, consisting of 3 wires arranged in parallel, inside a reconstruction region 54 indicated in the shape of a cuboid. The filters, which are assigned to the corresponding projections, are determined iteratively in a test measurement with the aid of such an arrangement.

Once these filters, or this set of filters, have/has been determined, the actual object to be scanned can be scanned under the same geometric conditions, and tomographic data can be calculated by these filters with the aid of the very fast FBP.

Figure 6:
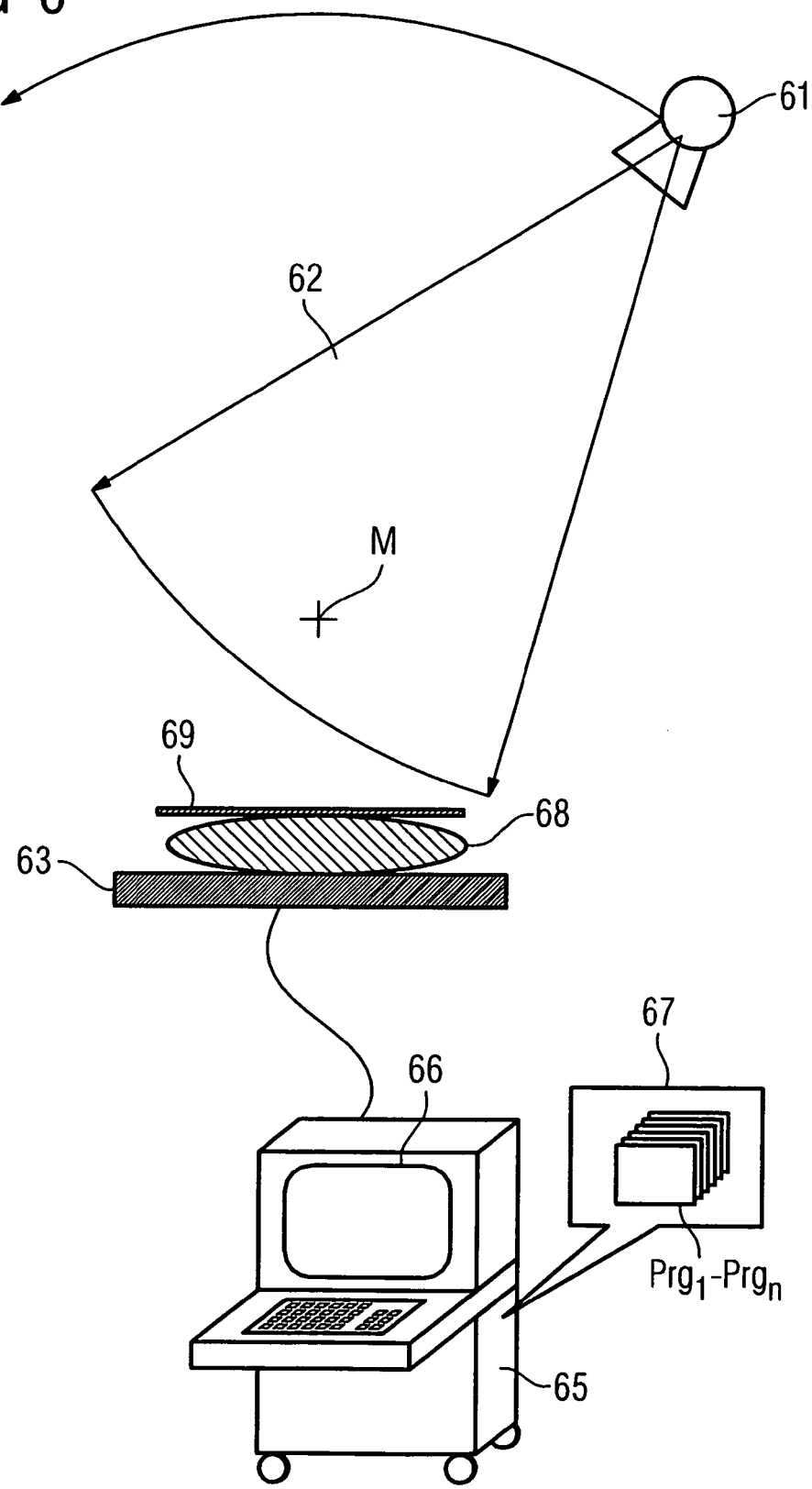
FIG. 6: shows a mammography system.

FIG. 6 shows this situation of a scan in a schematic sectional illustration. Here, a female thorax 68 is placed on the flat detector 63 and held by a compression plate 69 inside the reconstruction region (not shown in more detail). The x ray tube 61 moves on the circular path illustrated by an arrow above the center M such that the thorax 68 is scanned by the beam fan 62 swiveled in this way, and the absorption values are determined for a number of projection angles by the fixed flat detector, which has a multiplicity of detector elements (not illustrated here explicitly). The filters previously present in the memory 67 are called up in the computing unit 65 in accordance with previously recorded projections and are used to carry out an FBP. The programs $Prg_x$ required for this can likewise be present in the memory 67 and be called up as required. Owing to the high performance method, the reconstructed tomographic data can be displayed directly on the display screen 66 very quickly after the scan.

The method according to an embodiment of the invention can also be applied to the classic CT according to FIG. 1 and also to arrangements in which a number of detectors and radiation sources are used for the recording. Examples are aimed in the literature reference [KKK05] Kachelrieß M., Knaup M., Kalender W. A.: "Phase-Correlated Imaging from Multithreaded Spiral Cone-Beam CT Scans of the Heart", International Meeting on Fully Three-Dimensional Image Reconstruction, Salt Lake City; Utah, USA, Jul. 6-9, 2005; Proceedings of Fully3D pp. 159-162, the entire contents of which are hereby incorporated herein by reference.

It goes without saying that the abovementioned features of embodiments of the invention can be used not only in the respectively specified combination, but also in other combinations or on their own, without departing from the scope of the invention.

Still further, any one of the above-described and other example features of the present invention may be embodied in the form of an apparatus, method, system, computer program and computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a computer readable media and is adapted to perform any one of the aforementioned methods when run on a computer device (a device including a processor). Thus, the storage medium or computer readable medium, is adapted to store information and is adapted to interact with a data processing facility or computer device to perform the method of any of the above mentioned embodiments.

The storage medium may be a built-in medium installed inside a computer device main body or a removable medium arranged so that it can be separated from the computer device main body. Examples of the built-in medium include, but are not limited to, rewriteable non-volatile memories, such as ROMs and flash memories, and hard disks. Examples of the removable medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

Literature:
Bu04 Buzug: "Einführung in die Computertomographie" ["Introduction to computed tomography"], 1st edition 2004, Springer-Verlag, ISBN 3-540-20808-9
KS84 Kak, Slaney: "Principles of Computerized Tomographic Imaging", 1987, IEEE Press, ISBN 0-87942-198-3
OS75 Oppenheim, Alan V. Schafer, Ronald: "Digital Signal Processing", Prentice Hall, 1975, ISBN 0132146355
WZM04 T. Wu, J. Zhang, R. Moore, E. Rafferty, D. Kopans, W. Meleis, D. Kaeli: "Digital Tomosynthesis Mammography Using a Parallel Maximum Likelihood Reconstruction Method", Medical Imaging 2004: Physics of Medical Imaging, Proceedings of SPIE Vol., 5368 (2004) 1-11
KKK05 Kachelrieβ M., Knaup M., Kalender W. A.: "Phase-Correlated Imaging from Multithreaded Spiral Cone-Beam CT Scans of the Heart", International Meeting on Fully Three-Dimensional Image Reconstruction, Salt Lake City; Utah, USA, Jul. 6-9, 2005; Proceedings of Fully3D pp. 159-162.

What is claimed is:

1. A method for reconstructing a tomographic representation of an object from projection data of a moving radiation source through the object onto a detector, the method comprising:
   determining a filter via test projections and an iterative reconstruction technique using at least one identical spatial arrangement of the radiation source, the detector and a test object instead of the object to be scanned, for the given arrangement said filter resulting in an optimum filtering and back projection of the projection data of the test object for the tomographic representation;
   scanning the object, instead of the test object, in the given arrangement and determining projection data; and
   reconstructing the tomographic representation of the object using the determined projection data and the determined filter.

2. The method as claimed in claim 1, wherein at least one 2D sectional representation of the object is reconstructed.

3. The method as claimed in claim 1, wherein at least one 3D volumetric representation of the object is reconstructed.

4. The method as claimed in claim 1, wherein 1D projections are used for determining the filter and for the reconstruction.

5. The method as claimed in claim 1, wherein 2D projections are used for determining the filter and for the reconstruction.

6. The method as claimed in claim 1, wherein the projections are recorded using conical beam geometry.

7. The method as claimed in claim 1, wherein the projections are recorded using fan beam geometry.

8. The method as claimed in claim 1, wherein the projections are recorded using parallel beam geometry.

9. The method as claimed in claim 1, wherein a rebinning is carried out on the recorded data.

10. The method as claimed in claim 1, wherein the determined filter is spatially dependent.

11. The method as claimed in claim 1, wherein the object is scanned in an angular range less than or equal to 180 degrees.

12. The method as claimed in claim 1, wherein the object is scanned using an angular distance of at least 2 degrees between the projections.

13. The method as claimed in claim 1, wherein the scanning is performed with variable increment between the individual measured projections.

14. The method as claimed claim 1, wherein a dedicated filter is determined for each projection angle and is used for the reconstruction.

15. The method as claimed in claim 1, wherein a dedicated filter is determined for each projection site of at least one of the radiation source and the detector and is used for the reconstruction.

16. The method as claimed in claim 1, wherein measurements are carried out on at least one test object in order to determine the filter to be used.

17. The method as claimed in claim 1, wherein projections are calculated from a simulated test object in order to determine the filter to be used.

18. The method as claimed in claim 1, wherein a wire is used as a test object in order to determine the filter to be used.

19. The method as claimed in claim 1, wherein an arrangement of small balls is used as a test object in order to determine the filter to be used.

20. The method as claimed in claim 1, wherein a noise image is used as a test object in order to determine the filter to be used.

21. The method as claimed in claim 1, wherein noise is used as a given projection in order to determine the filter to be used.

22. The method as claimed in claim 1, wherein the filter to be used is firstly determined, then stored and not applied until later.

23. The method as claimed in claim 1, wherein a smaller number of new, averaged filters are calculated from the originally iteratively determined filters by averaging them over at least one of sites and projection angles.

24. The method as claimed in claim 1, wherein filters, for a at least one of a specific site and a specific projection, are calculated by interpolation between filters that belong to at least one of other sites and other projections.

25. The method as claimed in claim 1, wherein a plurality of at least one of detectors and radiation sources are used.

26. The method as claimed in claim 1, wherein projections are obtained from ultrasound imaging.

27. The method as claimed in claim 1, wherein projections are obtained from magnetic resonance imaging.

28. The method as claimed in claim 1, wherein projections are obtained from x-ray imaging.

29. The method as claimed in claim 1, wherein projections are obtained from optical imaging.

30. The method as claimed in claim 26, further comprising: a data memory in which the filters are stored long term.

31. The method as claimed in claim 26, wherein programs transmit the determined projection data and, the stored filters to a separate image computer.

32. The method as claimed in claim 26, further comprising: at least one of a plurality of detectors and radiation sources.

33. A tomography unit for reconstructing a tomographic representation of an object from projection data off a moving radiation source through the object onto a detector, the tomography unit comprising:
   means for determining a filter via test projections and an iterative reconstruction technique using at least one identical spatial arrangement of the radiation source, the detector and a test object instead of the object to be scanned, for the given arrangement said filter resulting in an optimum filtering and back projection of the scanned, for the given arrangement said filter resulting in an optimum filtering and back projection of the projection data of the test object for the tomographic representation;
   means for scanning the object, instead of the test object, in the given arrangement and determining projection data; and means for reconstructing the tomographic representation of the object using the determined projection data and the determined filter.

34. The tomography unit as claimed in claim 33, wherein projections are obtained from ultrasound imaging.

35. The tomography unit as claimed in claim 33, wherein projections are obtained from magnetic resonance imaging.

36. The tomography unit as claimed in claim 33, wherein projections are obtained from x-ray imaging.

37. The tomography unit as claimed in claim 33, wherein projections are obtained from optical imaging.

38. The tomography unit as claimed in claim 33, further comprising:

a data memory in which the filters are stored long term.

39. The tomography unit as claimed in claim 33, further comprising:

at least one of a plurality of detectors and radiation sources.

40. A computer readable medium including program segments for, when executed on a computer device of a tomography unit, causing the tomography unit to implement the method of claim 1.

* * * * *